(12) United States Patent
Kazi et al.

(10) Patent No.: US 6,206,820 B1
(45) Date of Patent: Mar. 27, 2001

(54) DEVICE FOR SUPPORTING CARDIAC FUNCTION HAVING ELASTIC FILLING CHAMBERS

(75) Inventors: Arif Kazi, Karlsruhe; Paul Volker, St. Ingbert; Peter Feindt, Homburg, all of (DE)

(73) Assignee: Fraunhofer Gesellschaft zur Foerderung der angewandten Forschung, Munich (DE)

( * ) Notice: Subject to any disclaimer, the term of this patent is extended or adjusted under 35 U.S.C. 154(b) by 0 days.

(21) Appl. No.: 09/051,768

(22) PCT Filed: Oct. 17, 1996

(86) PCT No.: PCT/DE96/01978

§ 371 Date: Jun. 17, 1998

§ 102(e) Date: Jun. 17, 1998

(87) PCT Pub. No.: WO97/14286

PCT Pub. Date: Apr. 24, 1997

(30) Foreign Application Priority Data

Oct. 18, 1995 (DE) .............................................. 195 38 796

(51) Int. Cl.[7] ..................................................... A61M 1/12

(52) U.S. Cl. .............................................. 600/16; 623/3.21
(58) Field of Search ........................... 600/16, 17; 623/3, 623/3.1, 3.16, 3.21; 601/153

(56) References Cited

U.S. PATENT DOCUMENTS

| 3,376,863 | | 4/1968 | Kolobow et al. . | |
| 5,119,804 | * | 6/1992 | Anstadt | 601/153 |
| 5,131,905 | | 7/1992 | Grooters . | |
| 5,749,839 | * | 5/1998 | Kovacs | 601/153 |
| 5,848,962 | * | 12/1998 | Feindt et al. | 600/17 |

FOREIGN PATENT DOCUMENTS

| 33 07 211 A1 | 3/1982 | (DE) . |
| 94/02101 | 2/1994 | (WO) . |
| 94/27552 | 12/1994 | (WO) . |

* cited by examiner

*Primary Examiner*—George R. Evanisko
(74) *Attorney, Agent, or Firm*—Evenson, McKeown, Edwards & Lenahan, P.L.L.C.

(57) ABSTRACT

A device for assisting the functioning of a heart has elastic filling chambers attached to an elastic cover which can be placed at least partially around the heart. The filling chambers can be repetitively filled and emptied to exert mechanical pressure on a region of a pumping chamber of the heart.

16 Claims, 1 Drawing Sheet

DEVICE FOR SUPPORTING CARDIAC FUNCTION HAVING ELASTIC FILLING CHAMBERS

BACKGROUND AND SUMMARY OF THE INVENTION

This application claims the priority of German patent document 195 38 796.1, filed Oct. 18, 1995 and PCT patent document PCT/DE96/01978 filed Oct. 17, 1996, the disclosures of which are expressly incorporated by reference herein.

The present relates to a device for supporting cardiac function having elastic filling chambers which exert mechanical pressure and act selectively on the left ventricle region. The chambers can be filled with a medium and evacuated via connection lines.

When the heart fails to pump, the problem is a muscle weakness of the left cardiac chamber, such that insufficient blood volume can be expelled from the heart into the main aorta, and maintaining circulation is no longer ensured. The causes of this pumping failure of the cardiac muscle are varied. For instance, after heart surgery, viruses, deficient coronary circulation including pump failure can lead to loss of cardiac function.

To support cardiac activity mechanically during or following surgery, a number of devices are known. By way of illustration, German patent document DE-33 07 211 A1 discloses a device that can be implemented for supporting the activity of the myocardium. This device is composed of a rigid-walled container housing surrounding at least partially the ventricular region of the myocardium. Pump chambers, which directly deform the cardiac wall at the corresponding sites, are provided on the interior side of the container housing. However, this known device has the drawback that the pressure propagation on certain ventricle regions continues within the organ to such an extent that cardiac regions on the opposite side corresponding to the pressure exerting centers are pressed against the rigid container wall, thereby possibly causing irreversible damage to the heart or the vessels. Moreover, the rigid container wall lastingly impairs the natural expansion behavior of the heart.

Generic pump systems which are able to support cardiac function and are positioned at the heart with the aid of flexible bands are also known. A device of this type is disclosed, for example, in U.S. Pat. No. 5,131,905. However, devices of this type have the disadvantage that the limited width of the attachment bands permits only insufficient fixation effects. Moreover, the edges of the bands rub on the surface of the heart and can lead to irreversible local damage to tissue. Furthermore, attachment of the bands about the beating heart for surgery is very difficult and complicated.

In order to avoid the aforementioned disadvantages, International patent document WO 94/27552 describes a device for supporting cardiac function. The device is provided with two approximately opposite filling chambers that are connected via a U-shaped, rigid rod between which the left ventricle region of the heart is located. A special advantage of this device is that upon compression of the left ventricle region by corresponding filling of the filling chambers, the other cardiac regions can expand without hindrance. Corresponding damage to the surface of the heart due to bruising occurring by way of illustration when hard shells are employed is prevented in this manner.

However, the above described device for supporting cardiac function has the disadvantage that some mobility remains between the filling chambers and the surface of the heart so that slipping of the device on the heart surface cannot be ruled out.

DESCRIPTION OF THE INVENTION

The object of the present invention is to provide an improved device for supporting cardiac function, with elastic filling chambers which are filled with a medium and evacuated via connection lines and which exert mechanical pressure selectively on the left ventricle region. The device according to the invention can be attached over a large surface to the heart so that, on the one hand, the heart's freedom of movement is not restricted and, on the other hand, the device is attached to the surface of the heart in such a way that it cannot slip.

This and other objects and advantages are achieved by the device for supporting cardiac function according to the invention, which includes an elastic cover that can be placed at least partially around the heart. The left wall of the device is provided with filling chambers in the region of the left ventricle, which chambers can also be detachably joined via suited connecting elements integrated in the wall of the elastic cover.

In a preferred embodiment of the invention, the filling chambers are located on the external side of the elastic cover, and possess expansion behavior directed predominantly toward the elastic cover. In this manner selective pressure can be exerted on the interior side of the elastic cover. For this purpose, for example, the side of the filling chamber facing the elastic cover is designed more elastic than the side facing in the opposite direction.

The invented elastic cover is provided at suitable sites, corresponding to the region of the left ventricle of the heart, with filling chambers (also composed of elastic material) which are integrated in the wall or joined thereto. The filling chambers preferably are integrated in pairs opposite each other in the wall of the elastic cover, and are provided with connecting valves, to which corresponding connecting lines can be applied. Alternatively, connecting elements, via which the filling chambers can subsequently be attached to the wall of the elastic cover, are integrated in the wall. Velcro connections, for example, are suitable for this purpose.

The material and size of the elastic cover must be selected so that, on the one hand, the heart can be covered snugly and, on the other hand, the expansion behavior of the heart remains unimpeded. That is, the cover must be so easily expandable that it imposes little or no impediment to expansion of the heart in a diastolic state, but remains sufficiently elastic in the diastolic state to present the cover from slipping on the surface of the heart.

An essential advantage of the intended embodiment of the cover is, in particular, that first the elastic cover is placed together with the elastic filling chambers attached to its wall, using suited auxiliary means, about the heart. After the elastic cover has been positioned at the heart in a suited manner and has fixed itself by means of its intrinsic elasticity to the heart, the connecting lines can be joined to the filling chambers. Abutment elements, described in the previously cited International patent document WO 94/27552, may also be attached at the sites of the filling chambers. Joining individual components which together yield a whole device for supporting cardiac function simplifies surgery substantially so that the actual surgical measures applied to the patient can be reduced considerably.

Other objects, advantages and novel features of the present invention will become apparent from the following

DETAILED DESCRIPTION OF THE DRAWINGS

Figure 1A:
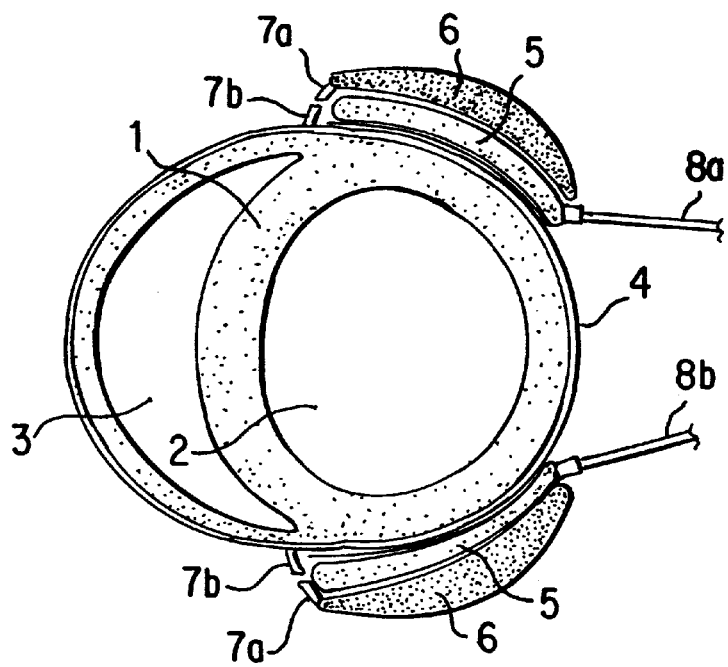
FIG. 1a is a schematic cross section of a heart in a diastolic state with the applied device for support cardiac function.

FIG. 1a shows a cross section of a heart 1 with an expanded left ventricle 2 and the right ventricle 3. An elastic cover 4, lying snugly on the external wall of the heart, is provided. This elastic cover is provided with two filling chambers 5 in a pressureless (emptied) state at two opposite sites in the region of the left ventricle 2.

Figure 1B:
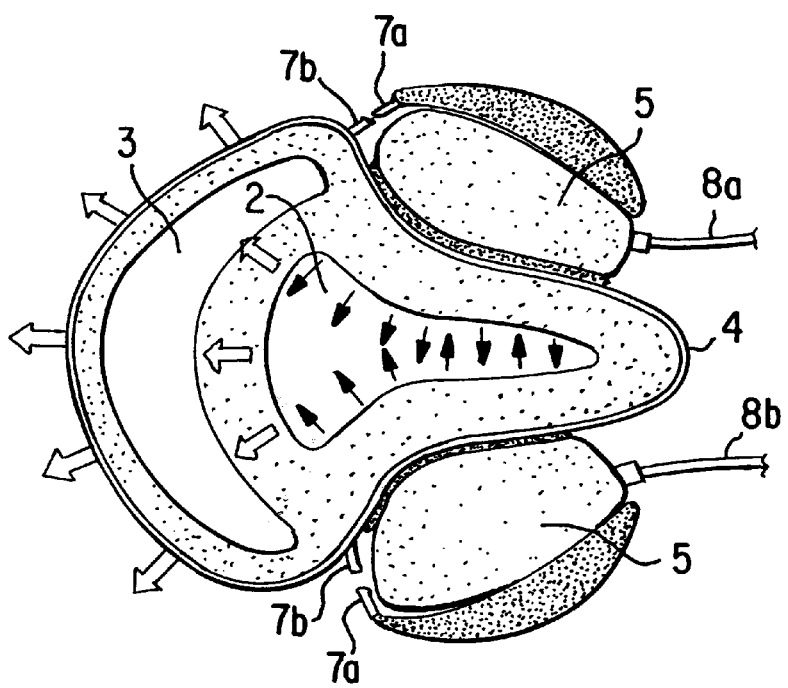
FIG. 1b is a corresponding cross section in a systolic state.

The filling chambers 5 are glued or molded onto the wall of the elastic cover at connections indicated schematically at 7a and 7b in FIGS. 1a and 1b. The filling chambers can also be designed separately and detachably connected via connecting elements, which are integrated in the wall, to the elastic cover.

Mechanical abutments 6, which are rigidly connected to each other via a rod (not shown), are provided over the respective filling chambers 5. Connecting valves, via which the filling chambers can be filled through connecting lines 8a, 8b and corresponding connections 9a, 9b, which are shown schematically in FIGS 1a and 1b.

FIG. 1b shows the heart 1 in a systolic state. That is, the left ventricle is laterally pressed together by the expansion of filling chambers 5. The fixed allocation of the filling chambers 5 to the external wall of the elastic cover prevents the pump system from slipping relative to the wall of the heart. The pressure action (indicated by the arrows in FIG. 1b) continues inside the heart through the walls of the heart 1 in the direction of the right ventricle, which can expand without hindrance due to the elastic property of the elastic covers 4.

As previously mentioned, the material of the elastic cover must, be selected such that, on the one hand, there is no lateral slipping of the elastic cover relative to the wall of the heart while on the other hand, the elastic cover has enough elasticity to follow the expansion behavior of the organ without hindrance.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A device for supporting the functioning of a heart, comprising:

an elastic supporting member adapted to be installed in place at least partially around the heart, with at least a portion of said elastic supporting member adjacent a pumping chamber of said heart;

elastic filling chambers mounted on said portion of said elastic supporting member for supporting said chambers in a fixed relationship to said heart to prevent slippage of said chambers relative to the wall of the heart; and connections for filling said filling chambers with a medium, and for evacuating said filling chambers, to exert selective mechanical pressure on a region of the pumping chamber ot the heart;

wherein said filling chambers are attached on said portion of said elastic supporting member by one of glue and a molded connection.

2. The device according to claim 1, wherein said supporting member has a size and elasticity to stretch onto and snugly engage said heart, held in fixed position thereon by elastic tension generated by stretching of said supporting member.

3. A device for supporting the functioning of a heart, comprising:

an elastic cover adapted to be installed in place at least partially around the heart, with at least a portion of said elastic cover adjacent a pumping chamber of said heart;

elastic filling chambers mounted on said portion of said elastic cover; and connections for filling said filling chambers with a medium, and for evacuating said filling chambers, to exert selective mechanical pressure on a region of the pumping chamber of the heart; and further comprising connecting elements on said elastic cover, and on said filling chambers, said filling chambers being detachably attached to said wall by said connecting elements.

4. The device according to claim 3, wherein said elastic cover is adapted to be installed with at least a portion of said elastic cover adjacent a left ventricle of said heart.

5. The device according to claim 4, comprising two filling chambers, arranged on said elastic cover, said two filling chambers being adapted to be disposed on opposing sides of the left ventricle.

6. The device according to claim 3, wherein said filling chambers are attached to an external side of said elastic cover.

7. The device according to claim 3, wherein:

said elastic cover is adapted to lie snugly on the heart whereby, in an installed state of said elastic cover, slipping of said elastic cover on the heart surface is avoided; and said elastic cover is sufficiently elastic not to impede the expansion efforts of the heart in a diastolic state.

8. A device according to claim 3, further comprising spacially fixed mechanical abutments arranged on a side of said filling chambers opposite said elastic cover and adapted to constrain expansion of said filling chambers in a direction opposite said elastic cover when said filing chambers are being filled with a medium, whereby expansion of said expansion chambers compresses the left ventricle.

9. A device for supporting the functioning of a heart, comprising:

an elastic cover adapted to be installed in place at least partially around the heart, with at least a portion of said elastic cover adjacent a pumping chamber of said heart;

elastic filling chambers mounted on said portion of said elastic cover for supporting said chambers in a fixed relationship to said heart to prevent slippage of said chambers relative to the wall of the heart; and connections for filling said filling chambers with a medium, and for evacuating said filling chambers, to exert selective mechanical pressure on a region of the pumping chamber of the heart.

10. The device according to claim 9, wherein said filling chambers are attached to an external side of said elastic cover.

11. The device according to claim 9, comprising two filling chambers, arranged on said elastic cover, said two filling chambers being adapted to be disposed on opposing sides of the left ventricle.

12. The device according to claim 9, wherein:

said elastic cover is adapted to lie snugly on the heart whereby, in an installed state of said elastic cover, slipping of said elastic cover on the heart surface is avoided; and said elastic cover is sufficiently elastic not to impede the expansion efforts of the heart in a diastolic state.

13. A device according to claim 9, further comprising spacially fixed mechanical abutments arranged on a side of said filling chambers opposite said elastic cover and adapted to constrain expansion of said filling chambers in a direction opposite said elastic cover when said filing chambers are being filled with a medium, whereby expansion of said expansion chambers comprises the left ventricle.

14. The device according to claim 9, further comprising:

connecting lines detachably coupled to said connections for filling chambers.

15. The device according to claim 9, wherein said cover has a size and elasticity to stretch onto and snugly engage said heart, held in fixed position thereon by elastic tension generated by stretching of said supporting member.

16. The device according to claim 9, wherein said elastic cover is adapted to be installed with at least a portion of said elastic cover adjacent a left ventricle of said heart.

* * * * *